United States Patent
Göckeritz et al.

(10) Patent No.: US 10,478,362 B2
(45) Date of Patent: Nov. 19, 2019

(54) DEVICE FOR REPOSITIONING BONE FRACTURE FRAGMENTS

(71) Applicant: MAQUET GMBH, Rastatt (DE)

(72) Inventors: Stefan Göckeritz, Remagen (DE); Thomas Krickeberg, Karlsbad (DE); Bernhard Katzenstein, Iffezheim (DE)

(73) Assignee: MAQUET GMBH, Rastatt (DE)

( * ) Notice: Subject to any disclaimer, the term of this patent is extended or adjusted under 35 U.S.C. 154(b) by 0 days.

(21) Appl. No.: 15/442,878

(22) Filed: Feb. 27, 2017

(65) Prior Publication Data

US 2017/0165142 A1    Jun. 15, 2017

Related U.S. Application Data

(63) Continuation-in-part of application No. PCT/EP2015/071489, filed on Sep. 18, 2015.

(51) Int. Cl.
*A61B 17/56* (2006.01)
*A61B 17/64* (2006.01)
(Continued)

(52) U.S. Cl.
CPC .......... *A61G 13/0036* (2013.01); *A61B 17/66* (2013.01); *A61B 34/74* (2016.02); *A61G 13/08* (2013.01); *A61G 13/1245* (2013.01); *B25J 1/00* (2013.01); *B25J 9/0087* (2013.01); *B25J 9/02* (2013.01); *B25J 9/12* (2013.01); *B25J 13/00* (2013.01); *A61B 2034/742* (2016.02)

(58) Field of Classification Search
CPC ............... A61G 13/0036; A61G 13/08; A61G 13/1245; A61B 17/66; A61B 34/74; A61B 2034/742; B25J 1/00; B25J 9/0087; B25J 9/02; B25J 9/12; B25J 13/00

USPC ................... 606/53–59, 86 A, 86 B
See application file for complete search history.

(56) References Cited

U.S. PATENT DOCUMENTS 5,827,283 A * 10/1998 Groiso ............... A61B 17/6408
                                              606/57
8,425,519 B2 * 4/2013 Mast .................. A61B 17/6408
                                              606/57

(Continued)

FOREIGN PATENT DOCUMENTS

DE            10209209 B4      3/2006
DE      102012112716 A1      6/2014
(Continued)

OTHER PUBLICATIONS

International Search Report dated Jan. 21, 2016 which issued for corresponding international application PCT/EP2015/071489, 3 pages.

*Primary Examiner* — Pedro Philogene

(57) ABSTRACT

A device for repositioning bone fracture fragments is disclosed. The device has a carrier assembly and a first arm assembly attached to the carrier assembly, the first arm assembly configured to hold a first bone fracture fragment. The device also has a second arm assembly attached to the carrier assembly, the second arm assembly configured to hold a second bone fracture fragment. The device further has an actuator assembly configured to adjust the second arm assembly, and an operating assembly configured to control an adjustment of the second arm assembly via the actuator assembly. The operating assembly is a manually operatable operating assembly.

21 Claims, 13 Drawing Sheets

(51) Int. Cl.
*A61B 17/66* (2006.01)
*A61G 15/00* (2006.01)
*A61G 13/00* (2006.01)
*A61B 34/00* (2016.01)
*A61G 13/08* (2006.01)
*A61G 13/12* (2006.01)
*B25J 1/00* (2006.01)
*B25J 9/00* (2006.01)
*B25J 9/02* (2006.01)
*B25J 9/12* (2006.01)
*B25J 13/00* (2006.01)

(56) References Cited

U.S. PATENT DOCUMENTS

| | | | |
|---|---|---|---|
| 8,702,705 B2 * | 4/2014 | Ziran | A61B 17/66 606/57 |
| 2013/0218216 A1 | 8/2013 | Mast et al. | |
| 2013/0296882 A1 * | 11/2013 | Kim | A61B 34/70 606/130 |
| 2015/0323398 A1 * | 11/2015 | Lauzier | B25J 9/0081 73/862.08 |

FOREIGN PATENT DOCUMENTS

| | | |
|---|---|---|
| EP | 2436324 A1 | 4/2012 |
| WO | 2006/126167 A2 | 11/2006 |
| WO | 2010/138715 A1 | 12/2010 |
| WO | 2013/130023 A1 | 9/2013 |

\* cited by examiner

DEVICE FOR REPOSITIONING BONE FRACTURE FRAGMENTS

CROSS REFERENCE TO RELATED APPLICATIONS

The present application is a continuation-in-part filed under 35 U.S.C. § 111(a), and claims the benefit under 35 U.S.C. §§ 365(c) and 371 of PCT International Application No. PCT/EP2015/071489, filed Sep. 18, 2015, and which designates the United States of America, and German Patent Application No. 10 2014 113 658.6, filed Sep. 22, 2014. The disclosures of these applications are herein incorporated by reference in their entirety.

TECHNICAL FIELD

The disclosure relates to a device for repositioning bone fracture fragments, which may comprise a carrier unit, a first arm attached to the carrier unit for holding a first bone fracture fragment and a second arm attached to the carrier unit for holding a second bone fracture fragment.

BACKGROUND

The repositioning and stabilization of the fragments are typically unplanned surgical procedures. If the patient's condition (e.g., the patient's circulation) is stable, the operator will usually treat the fracture without making use of various aids. Generally, depending on the fracture and number of fragments, different osteosynthesis materials and methods are used. Both plates and intramedullary nails are commonly used. So that the intramedullary nail or the plate can be correctly applied, the fragments have to be aligned and/or repositioned with regard to each other. The quality of the alignment may not be changed post-operatively. For correction purposes the typical option is a further medical procedure. As the bone fragments lie inside the soft tissue of the extremities, they can be accurately repositioned with the help of X-ray image intensifiers. An additional difficulty is the fact that the muscles surrounding the bone contract so that the fragments end up in an unnatural alignment.

In order to correctly align the fragments, forces are applied to the fragments from outside. These are kept constant for the duration screwing the plates or inserting the intramedullary nails.

Imprecise alignment of the fragments results in rather large rotative misorientation of the fragments with regard to each other which can no longer be changed postoperatively. Due to the high cost and medical risk of a corrective procedure, rotative misorientations are largely tolerated, resulting in unsuitable treatment of the patient.

An initial possibility for aligning the bone fracture fragments is to give an assistant physician the task of exerting the forces and repositioning the fragments by pulling and aligning the distal end of the extremity. During this, the operator aligns and fastens the osteosynthesis material with the aid of an X-ray image intensifier. In doing so the assistant physician and operator stand very close to a source of X-rays for a longer period and are therefore exposed to increased radiation. Particularly because of constant small movements by the assistant physician, the X-ray image is constantly updated.

The problem with this is that alignment of the bones can take place with a rotative error which is not detected during the operation. A malposition of up to 15° is therefore considered as acceptable. For the patients, this amounts to for example internal/external rotation of the foot of up to 15°, which postoperatively can lead to complications or increased wearing of the joint.

In the case of a fracture of the lower extremities, a patient can also be placed on an extension table and the distraction forces exerted on the patient via this. The advantage of this is that the repositioning of the extremity is considerably more stable.

A drawback is that pre-operative positioning is laborious and partially contra-indicated in the case of patients with multiple traumas. There have also been reports of unsuitable effects to the nervous system and soft tissue lesions in the perineum. A further possibility is the use of a mechanical external fixator. This is a mechanical device with which the fragments are fixed to each other by means of Schanz screws/Kirschner wires via extracorporeal rods. Systems are known in which the rods can be adjusted by spindles.

A further possibility is the use of robotic assistance systems. Here, usually the distal fragment of the fracture fragments is positioned via suitable fastening or gripper systems in relation to the proximal fragment by way of a robotic system. The disadvantage of this is that this is a time-consuming procedure as the robots (as well as an appropriate optical navigation system) are initialized and registered. In most cases, these processes require 3D X-ray images which can only be produced by CT. Such techniques can therefore be used if 3D X-ray images with reference bodies are available, specialists who can proficiently operate the systems are present on site, and the patient's condition is not at risk/is stable.

SUMMARY OF THE DISCLOSURE

In at least some exemplary embodiments, a device for the repositioning of bone fracture fragments with the help of which accurate repositioning of the bone fracture fragments in a simple manner is provided.

In at least some exemplary embodiments, the device array have an electric actuator unit for adjusting the second arm. The device also have an operating element for controlling the adjustment of the second arm via the electric actuator unit.

Accordingly in at least some exemplary embodiments, repositioning of the bone fracture fragments relative to each other can be automatically carried out by the device in a simple manner. For this, the first bone fracture fragment may be fastened to the first arm and the second bone fracture fragment to the second arm. Via the actuator unit, with the aid of the operating unit, the second bone fracture fragment may then be moved into the required position in a motorized manner.

This has the advantage that the forces required for repositioning are not exerted manually, through which a relatively more precise repositioning can take place, thereby preventing unsuitable positions. In addition, no persons would be present in the X-ray area during the repositioning.

Compared with robotic systems the device has the advantage that it is of simpler and compact construction.

In at least some exemplary embodiments, on the end of the first arm facing away from the carrier unit, a first holder unit for holding Schanz screws and/or, on the end of the second arm facing away from the carrier unit, a second holder unit for holding Schanz screws may be provided. In this way the Schanz screws previously inserted into the bone fracture fragments can be fastened to the arms in a simple manner, so that via alignment of the arms relative to each other the bone fracture fragments held by the Schanz screws can then be brought into the desired position.

In at least some exemplary embodiments, with the help of the actuator unit, the second arm may be adjustable in such a way that the position of the second actuator unit relative to the carrier unit can be adjustable at will, e.g. in all directions if possible.

In at least some exemplary embodiments, with the help of the actuator unit the second arm can be adjusted in position and alignment in such a way that the second holder unit is adjustable about all six degrees of freedom of three-dimensional space. The second holder unit can thus be moved along three axes orthogonally positioned with regard to each other and also be turned about all three axes. This achieves that substantially any desired alignment of the bone fracture fragments may be possible so that substantially every desired position can be set.

The carrier unit may also comprise a fastening unit for fastening the device to an operating table. This has the advantage that the device can be attached to the appropriate operating table when desired. For example, the device may be designed in such a way that a friction connection is produced so that when the patient's position is changed the forces remain approximately constant.

The fastening unit may also be designed in such a way that it has an articulated joint through which the device can be turned about at least one axis relative to the operating table, so that, more particularly, the legs can be splayed accordingly.

The fastening unit may also be designed in such a way that the device can be attached to standard interfaces for holding leg plates.

In at least some exemplary embodiments, the first arm may have at least one manually adjustable articulated joint. Preferably, several manually adjustable articulated joints may be provided. The position and alignment of the first holder unit can also be changed, so that the necessary positioning of the first bone fracture fragment can take place. For example, manually operated securing assemblies (e.g., securing units) may be provided on the articulated joints to secure the articulated joints, so that after manual alignment of the first arm this can be fixed in the desired position.

The first arm may thus be purely manually adjustable. In an alternative exemplary embodiment of the disclosure, a further electric actuator unit, for example one motor or more motors, can be provided for adjusting the first arm.

The articulated joint (s) of the first arm may be designed so that the first holder unit can be adjusted about six degrees of freedom.

The first arm can, more particularly, be an arm as is described in German patent application DE 10 2012 112 716 A1 and US patent application US20150297305 A1. The design and function of the arms may be similar to the arm disclosed in German patent application DE 10 2012 112 716 A1 and US patent application US20150297305 A1. US patent application US20150297305 A1 is hereby incorporated by reference.

In at least some exemplary embodiments, the carrier unit may have a rail, and the second arm may have a slide which is arranged on the rail to move in the direction of the longitudinal axis of the rail. Movement of the slide, and thus of the second arm on the rail may take place for example with the aid of the electric actuator unit.

The electric actuator may have a first motor, which engages with a spindle via which the slide can be moved along the rail.

In at least some exemplary embodiments, the second arm may also have several articulated joints, wherein each articulated joint is assigned a motor for adjusting the articulated joint. More particularly, these motors of the electric actuator unit may be each arranged directly on the articulated joint so that no elaborate force transmission over longer distances, which would lead to susceptibility to unsuitable operation and contamination, may be involved.

In at least some exemplary embodiments, the second arm may have a first, a second as well as a third articulated joint. The second arm may also have at least two connection plates. The first articulated joint may connect the first connection plate to the slide in an articulated manner, The first connection plate may be arranged between the first and the second articulated joint, wherein the second articulated joint may connect the first and the second connection plate to each other in an articulated manner. Arranged on the end of the second connection plate facing away from the second articulated joint is the third articulated joint, to which, in turn, the second holding unit may be fastened.

Hereby, in a relatively simple and compact fashion, a robust arm may be provided that is adjustable in a motorized manner and provides movement of the second holder unit and thus of the second bone fracture fragment in (for example) all six degrees of freedom of three-dimensional space.

The electric actuator unit controlling the operating unit for adjusting the second arm may be, for example, arranged in the region of the third articulated joint and may thus be located on the end of the second arm facing away from the carrier unit.

The operating unit may be designed in such a way that, when operated in a predetermined direction, the second arm may be moved/turned in this direction accordingly. Through being fastened on the end of the second arm, intuitive control may be achieved, e.g. the operator may move the operating element in the way that the second arm is to be moved. In this way, substantially precise adjustment of the second arm may be possible without involving a significant training and experience.

In at least some exemplary embodiments, the first articulated joint may be a unidirectional joint, e.g. with the first articulated joint permitting rotation about a first rotational axis. The second articulated joint may also be unidirectional and thus allow rotation about a second rotational axis. For example, the first and second rotational axes may in parallel to each other.

For example, the third articulated joint Wray be designed in such a way that it allows rotation about three axes of rotation arranged orthogonally with regard to each other. For example, one of these three axes of rotation may be aligned in parallel to the first and the second axis of rotation. Thus, via these three simply and stably constructed articulated joints adjustment in five degrees freedom may be possible. The sixth degree of freedom may be made possible by the movement of the slide, and thus of the second arm on the rail.

In at least some exemplary embodiments, the operating element may comprise a joystick which allows simple d intuitive operation. For example, the operating element itself may have six degrees of freedom so that, on operating the operating element about one of these degrees of freedom of the arm, the bone fracture fragment may also move about this degree of freedom in a corresponding manner. The operating element may be a 6 DoF sensor (e.g., 6 degree of freedom sensor) which makes operating input for controlling six degrees of freedom simple.

Additionally, In at least some exemplary embodiments, an upper leg cushion for supporting an upper leg and/or a lower leg cushion for supporting a lower leg may be attached to the carrier unit. More particularly, the fastenings of the cushions may be designed so that the cushions can be removed. Thus, after some steps or every step of the operation, for example, the insertion of an intramedullary nail, suitable support of the broken leg can take place or suitable access to the leg may be provided. Also for example, at least one device of the aforementioned type may be detachably fastened to an operating table. For example, the device may be fastened to the operating table via a friction-type fastening.

BRIEF DESCRIPTION OF THE DRAWINGS

Further features and advantages of the disclosure are set out in the following description which illustrates exemplary embodiments of the present disclosure.

FIG. 9 shows a schematic, perspective view of the arrangement in accordance with. FIGS. 4 to 8 with the upper leg cushion and lower leg cushion in place.

DETAILED DESCRIPTION AND INDUSTRIAL APPLICABILITY

Figure 1:
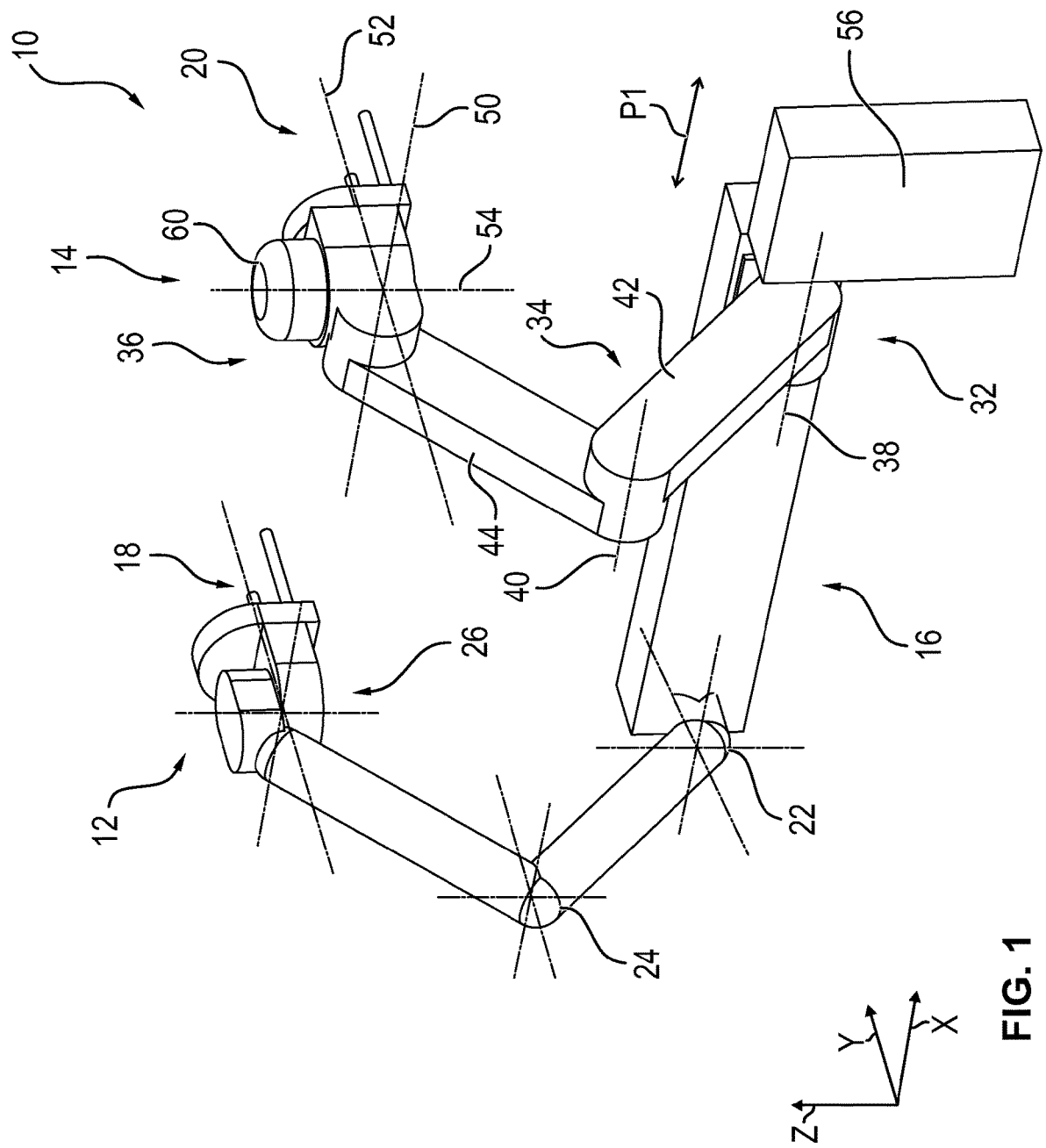
FIG. 1. shows a schematic, perspective view of an exemplary device for repositioning bone fracture fragments.
Figure 2:
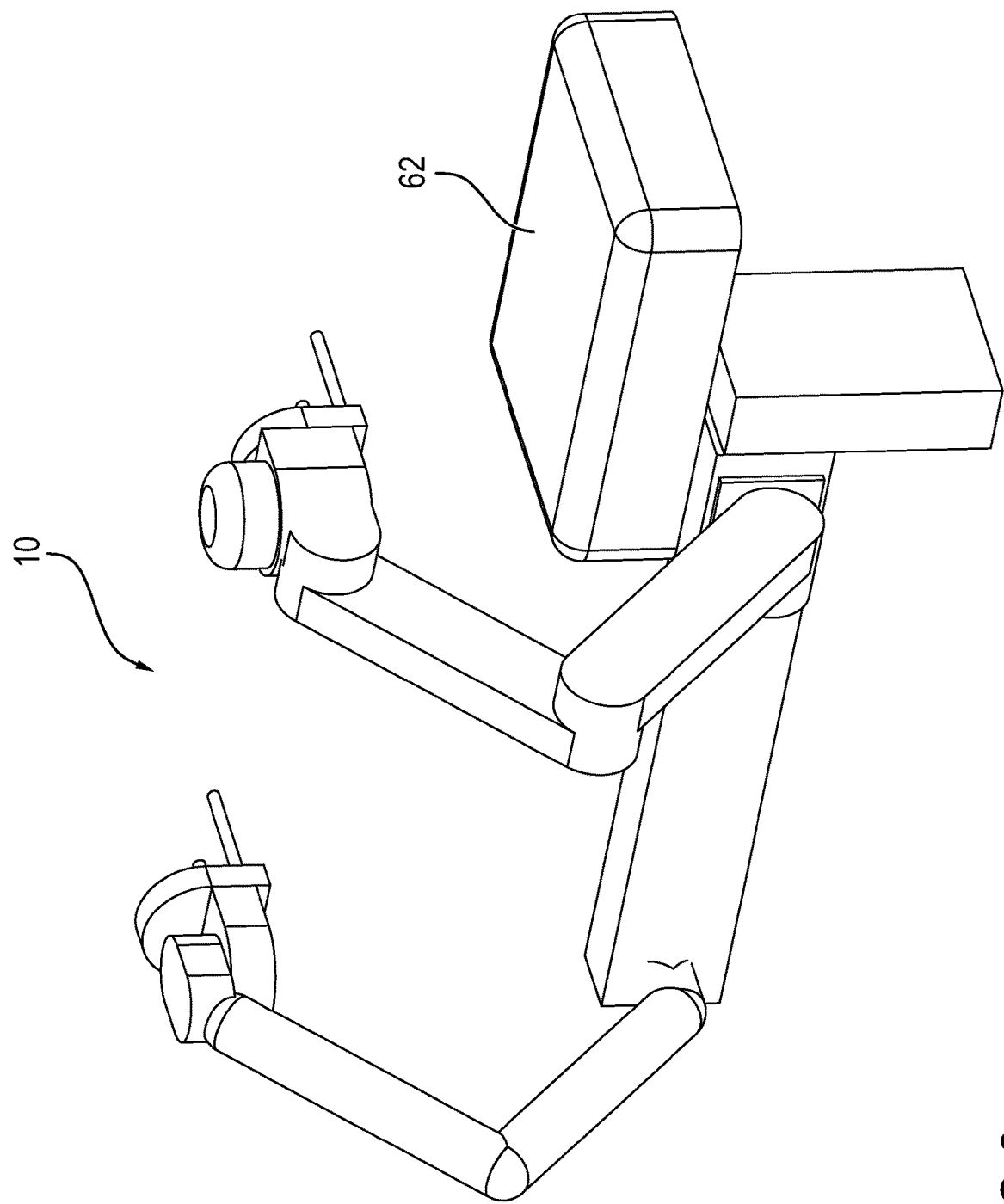
FIG. 2 shows a further schematic, perspective view of the exemplary device in accordance with FIG. 1.
Figure 3:
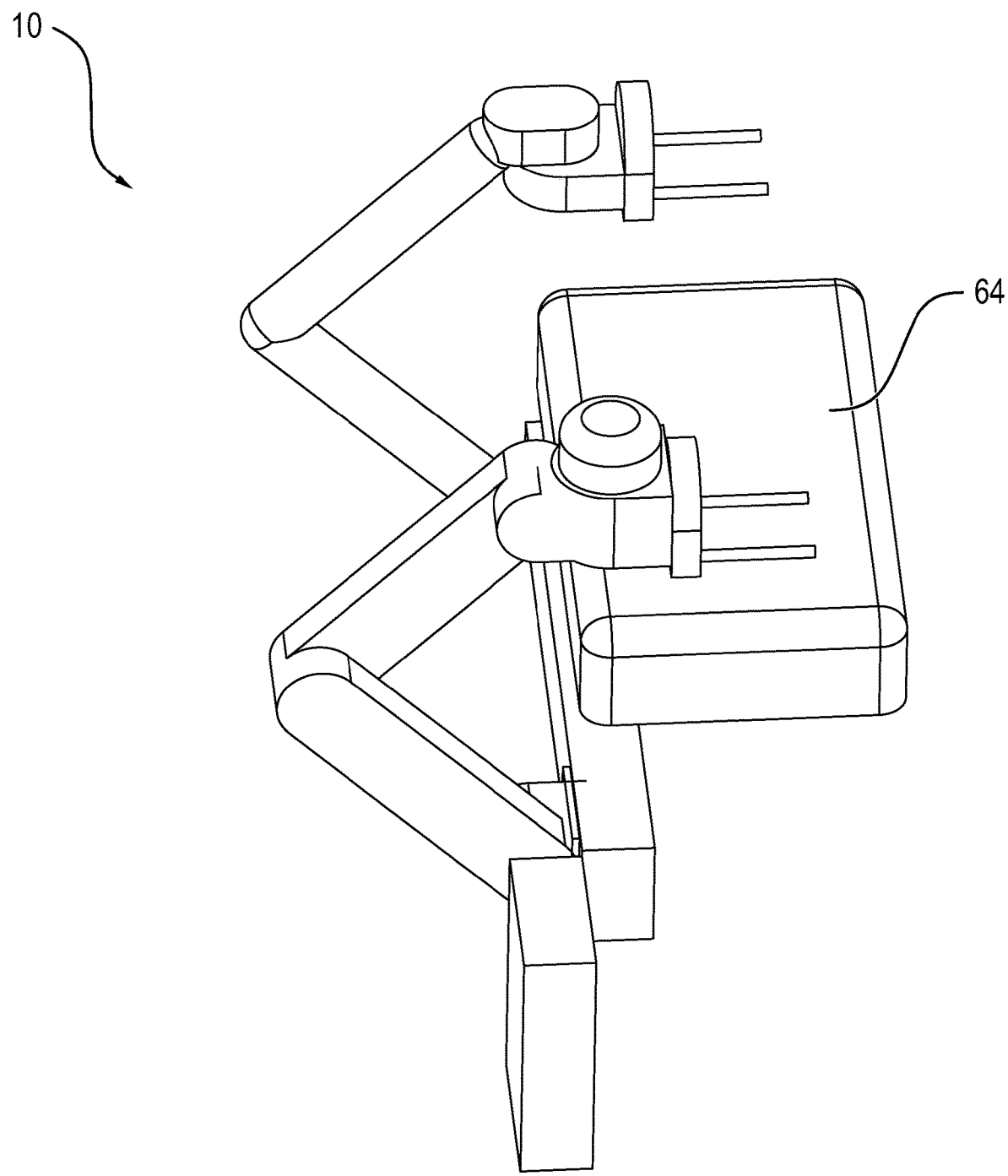
FIG. 3 shows a further schematic, perspective view of the exemplary device in accordance with FIGS. 1 and 2.
Figure 4:
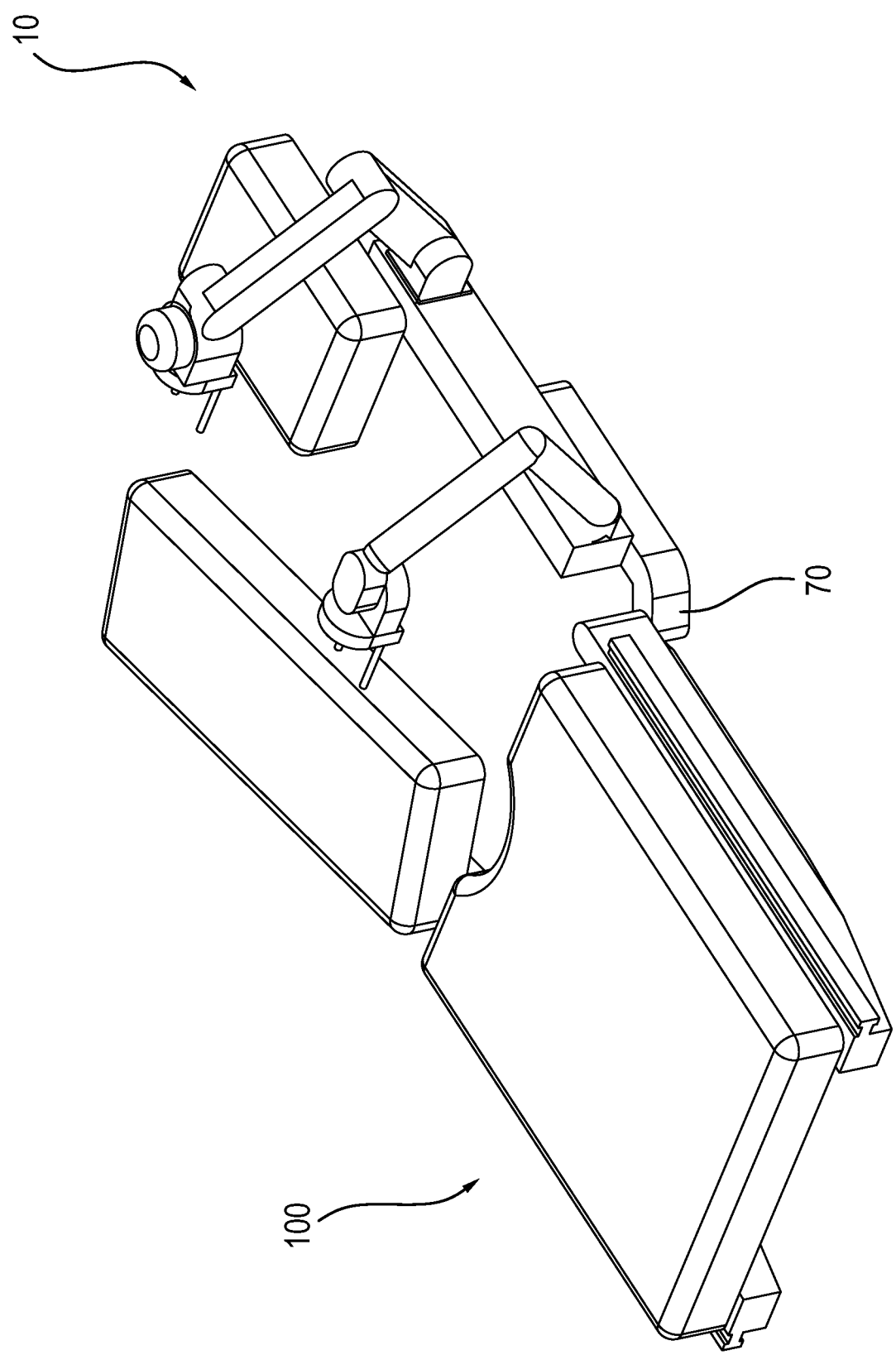
FIG. 4 shows a schematic view of an arrangement with a section of an operating table and the exemplary device in accordance with FIGS. 1 to 3.

FIGS. 1 to 3 each show a schematic, perspective view of a device 10 for repositioning bone fracture fragments.

In fractures of human bones, more particularly of large hollow bones, the fragments are aligned/repositioned with regard to each other. Only after this has been done can the bone fragments be fixed by, for example, plates and/or intramedullary nails. For repositioning the bone fracture fragments, the device 10 may comprise a first arm assembly (e.g., first arm 12) as well as a second arm assembly (e.g., second arm 14), a first end of each of which is attached to a carrier assembly (e.g., carrier unit 16). On the end portions (e.g., ends) opposite the carrier unit 16, a respective holder assembly (e.g., holder unit 18, 20) may be arranged, to which Schanz screws inserted into the bone fracture fragments can be fastened.

Initially, the Schanz screws of a first bone fracture fragment may be fastened to the first arm 12, for example to the first holder unit 18. The first holder unit 18, and thereby the first bone fracture fragment attached to it, may then be brought into the desired position. For this the first arm 12 may have three articulated joints 22, 24, 26 which may be manually adjustable. More particularly, the articulated joints 22, 24, 26 may be designed so that the first holder unit 18, and hence the bone fracture fragment attached to it, can be moved all three spatial directions as well as turned in three directions. In this way the alignment of the first bone fracture fragment can be changed as desired.

The second bone fracture fragment may then be attached via Schanz screws to the second holder unit 20 and aligned with the help of the second arm 14.

The second arm 14 may have three articulated joints 32, 34, 36, via which the position and alignment of the second holder element 20 can be varied.

The first articulated joint 32 may be a unidirectional joint that enables rotation about a first axis of rotation 38. The second articulated joint 34 may also be unidirectional and may allow rotation about a second rotational axis 40. A first connection plate 42 may be arranged between the first and the second articulated joint.

In addition, a second connection plate 44 may be arranged on the second articulated joint 40, via which the second articulated joint 34 may be articulately connected to the first connection plate 42. Arranged on the end of the second connection plate 44 facing away from the second articulated joint may be the third articulated joint 36.

The third articulated joint 36 may be designed as an articulated joint assembly with three separately-driven individual articulated joints, so that the articulated joint 36 may allow rotation about three axes of rotation 50, 52, 54 arranged orthogonally with regard to each other.

For example, the axes of rotation 38, 40 and 50 may be arranged in parallel with each other. For example, via the three articulated joints 32 to 36, adjustment about five degrees of freedom may be provided.

In order to also allow adjustment about the sixth degree of freedom, the end of the second arm 14 facing away from the second holder unit 20 may be disposed (e.g., arranged) on a slide member (e.g., slide) which can be moved on a rail member (e.g., rail) of the carrier unit 16 in the direction of the double arrow P1.

Both the movement of the second arm 14 on the rail of the carrier unit 16 and the adjustment of the articulated joints 32 to 36 may take place via electric actuators which may be controlled by an actuator assembly (e.g., an actuator unit 56 such as for example an electric actuator unit, a hydraulic actuator unit, or a motorized or mechanical actuator unit).

In at least some exemplary embodiments, the first articulated joint 32 and/or the second articulated joint 34 can also be in the form of an articulated joint assembly so that movement about more than one axis of rotation may be possible for these joints.

In addition to the mechanical assembly described and shown in the figures, the device 10 may comprise a control and operating unit with an operating assembly (e.g., an operating element 60), the actuator unit 56 and the electric actuators. The electric actuators may each have suitable motor transmission combinations. More particularly, a first electric actuator for moving the second arm 14 on the rail of the carrier unit 16 may be provided. In addition, five further electric actuators may be present, wherein each of these actuators is for adjusting one of the articulated joints 32 to 36 and arranged directly on it.

Furthermore, arranged on the end of the second arm 14 on which the holder unit 20 is also arranged, may be an operating element 60 via which the (e.g., electric, hydraulic, or mechanical) actuator unit 56 is controlled, so that via this operating element 60 the adjustment of the second arm 14 can be controlled by the operator.

The operating element 60 may be a 6 DoF (degrees of freedom) sensor, which itself can be operated in six degrees of freedom, wherein on operation of the sensor about one of these degrees of freedom the second arm may be moved accordingly, so that intuitive control is possible.

The cap of the operating element 60 can, for example, be moved in the direction of the three axes 50, 52, 54, which may result in a corresponding movement of the second holder unit 20 and thus of the second bone fracture fragment. In addition, the cap can be turned and tilted in two directions, which may be converted into a corresponding rotary movement.

Depending on which treatment of the fracture may be being carried out, different positioning of the broken extremity before, during and after the operation may occur. For example, various cushions can be applied to and also removed from the carrier unit 16. This may be advantageous in order to allow intraoperative access to the fracture and to remove objects that negatively affect the X-ray image to be removed from the direct radiation beam.

For example as shown in FIG. 1, no cushion is fastened to the carrier unit 16. In the embodiment shown in FIG. 2, also for example, a lower leg cushion 62 may be provided. The embodiment in FIG. 3 shows an upper leg cushion 64 (e.g., firmly) fastened to the carrier unit 16. Alternatively for example, both cushions 62, 64 can be provided.

As shown in FIGS. 4 to 9, the device 10 can be fastened to an operating table 100. For this, the device 10 may have a fastening assembly (e.g., fastening unit 70), which, in particular, allows articulated fastening to the operating table 100 by a friction-type connection.

Figure 5:
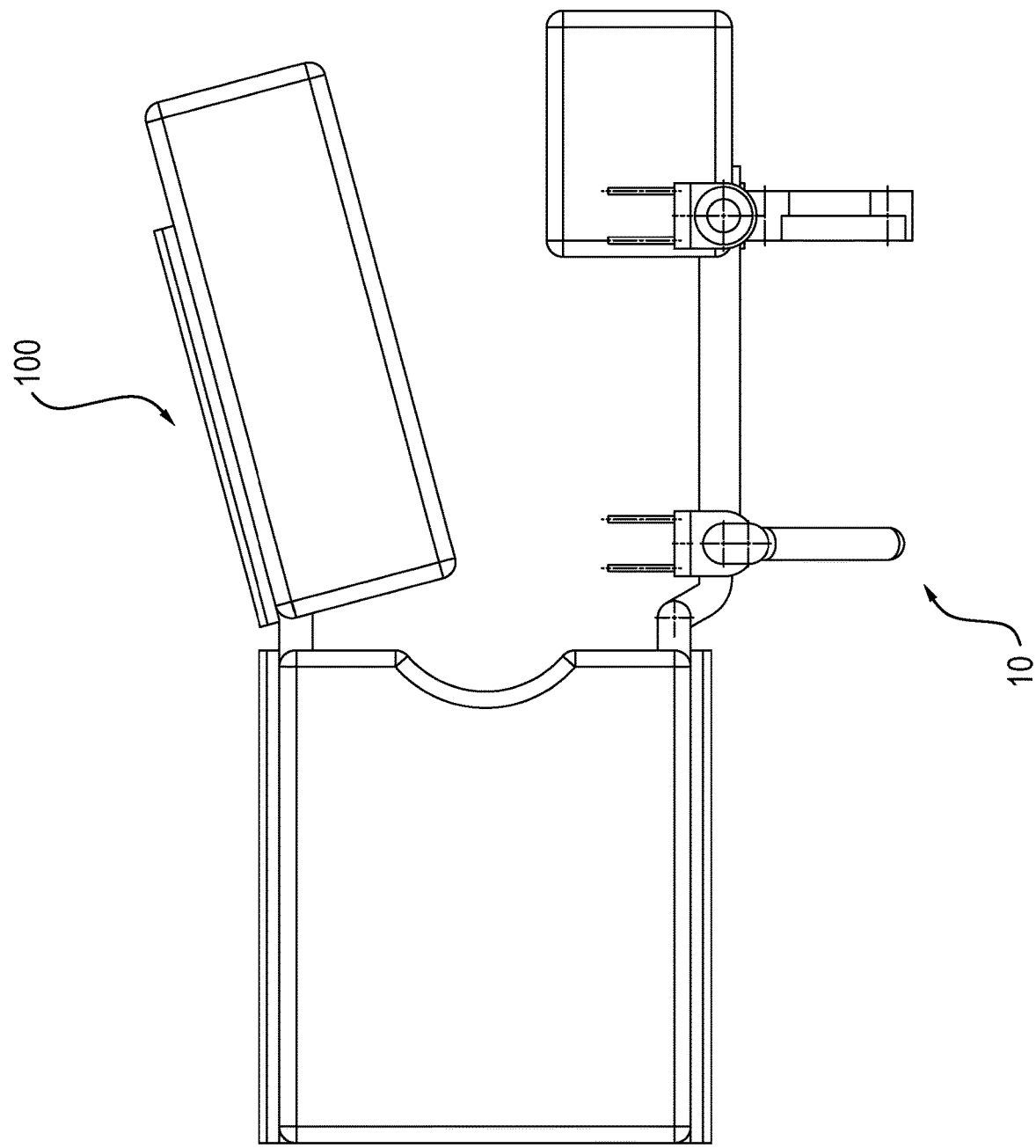
FIG. 5 shows a view from above of the arrangement in FIG. 4.
Figure 6:
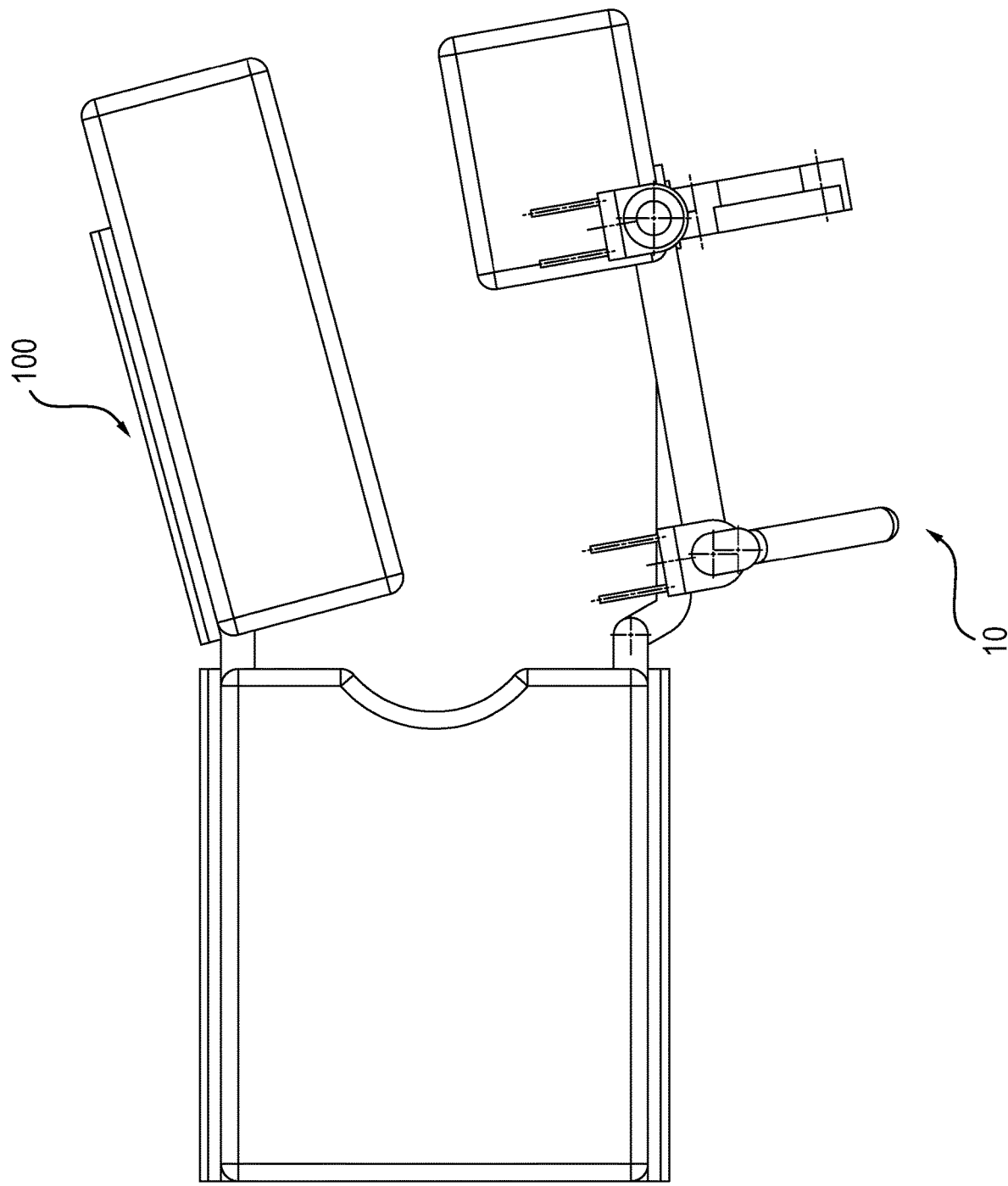
FIG. 6 shows a view from above of the arrangement in FIGS. 4 and 5 with changed orientation of the device for repositioning the bone fracture fragments.

As can be seen in FIGS. 5 and 6, the connection between the operating table 100 and the device 10 may be such that swiveling of the device 10 is possible, so that the leg placed on it can be positioned accordingly.

Figure 7:
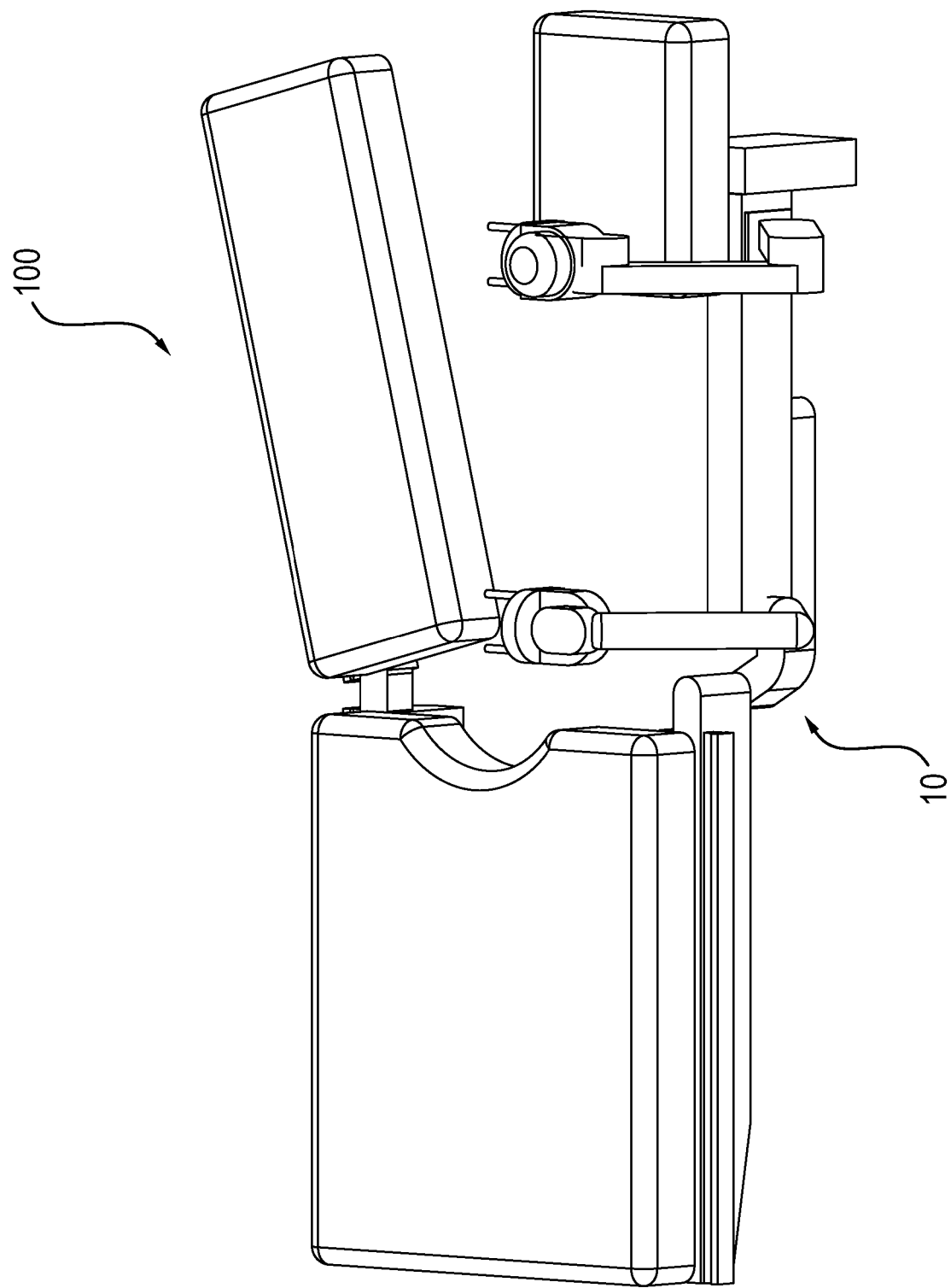
FIG. 7 shows a schematic, perspective view of the arrangement in accordance with FIG. 5.
Figure 8:
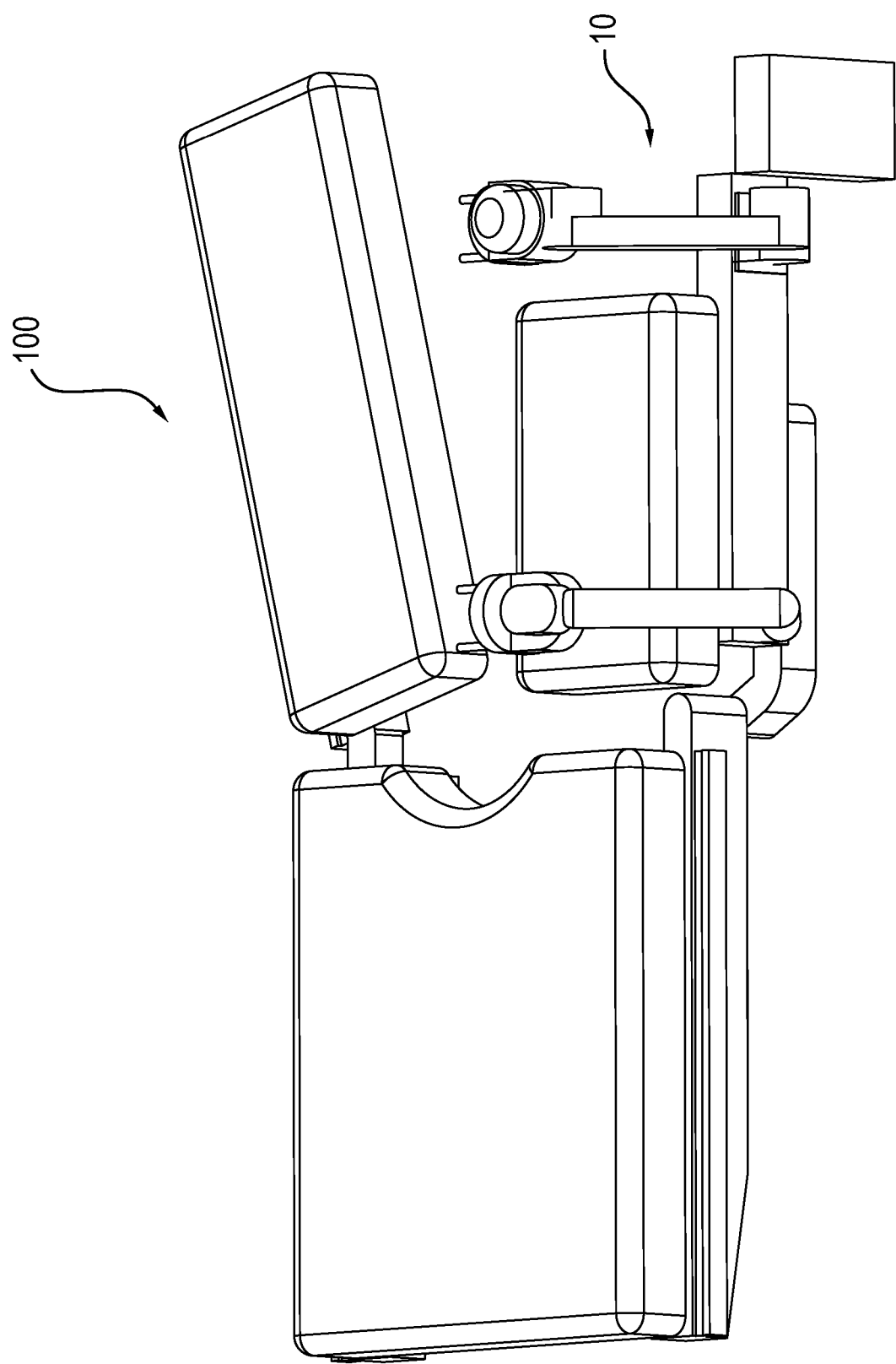
FIG. 8 shows a further schematic, perspective view of the arrangement in accordance with FIGS. 4 to 6 with the upper leg cushion in place.
Figure 9:
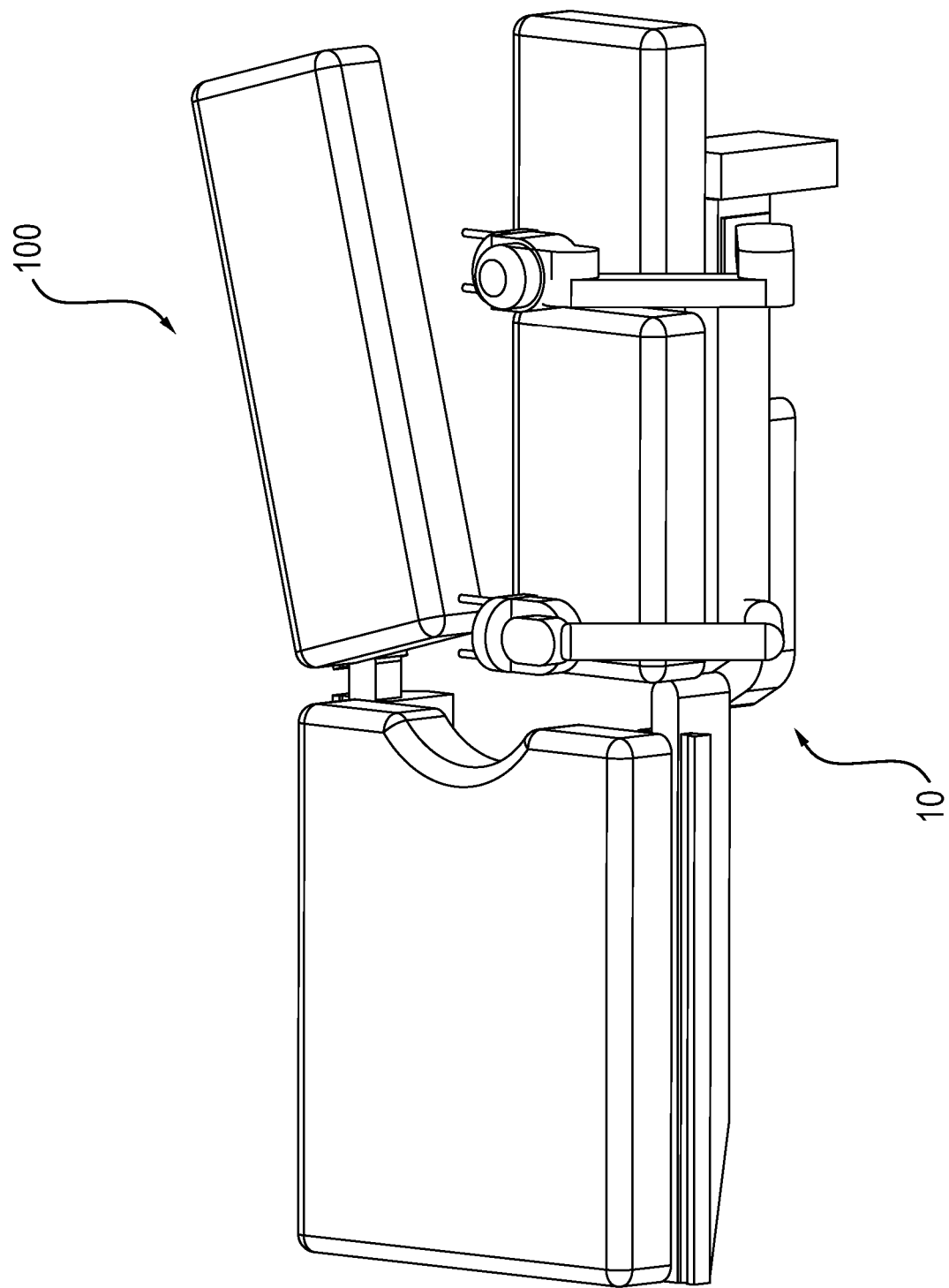
Figure 10:
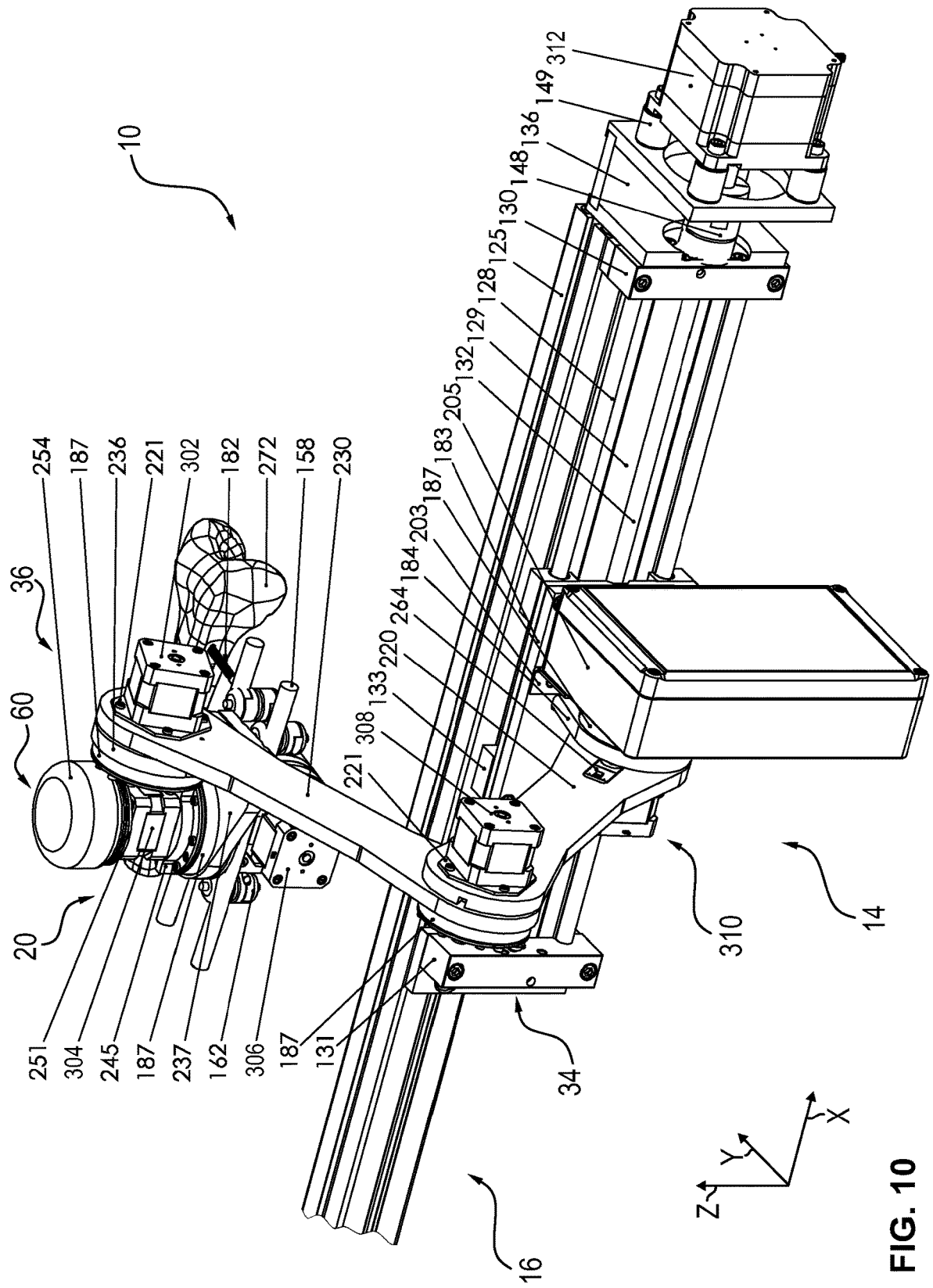
FIG. 10 shows a perspective detailed view of the exemplary device in accordance with FIGS. 1 to 3.
Figure 11:
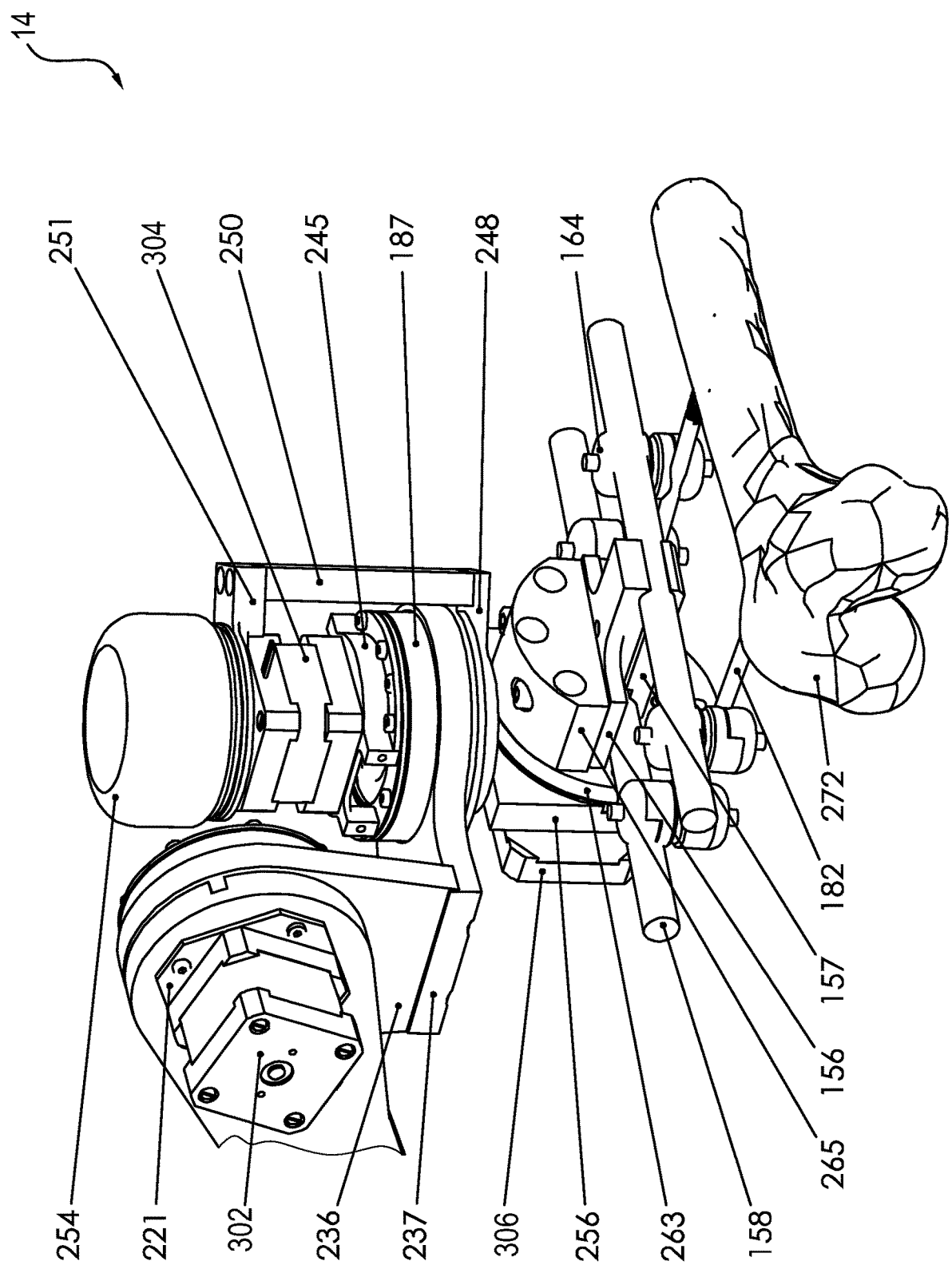
FIG. 11 shows a further perspective detailed view of the exemplary device in accordance with FIGS. 1 and 3.
Figure 12:
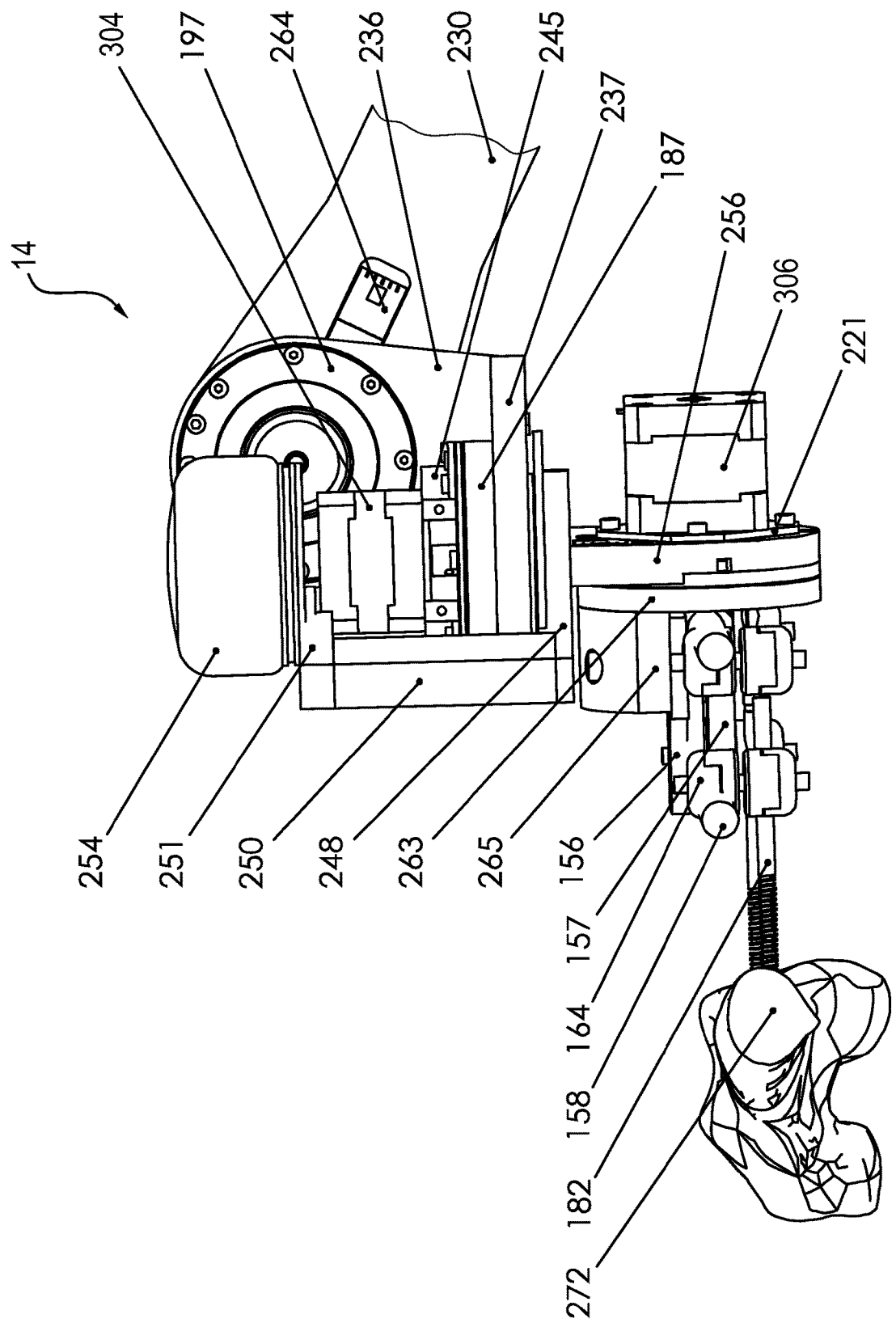
FIG. 12 shows a further detailed view of the exemplary device in accordance with FIGS. 1 to 3.

In FIGS. 7 to 9, further embodiments are shown, wherein a different exemplary combination of the applied cushions 62, 64 is shown in each embodiment FIGS. 10 to 12 each show detailed exemplary views of the device 10, wherein in FIG. 10 the second arm 14, a part of the carrier unit 16 and the rail of the carrier unit 16 are shown. FIGS. 11 and 12 each show the third articulated joint 36 as well as the second holding unit 20. A component of the device may be a linear track. The linear track may be aligned with its main axis along the X-axis of the coordinate system of the device 10. The Y-axis, which may be perpendicular to the X-axis, may point in the depth direction. The Z-axis, perpendicular to the other two axes, may point upwards.

The track may comprise a support structure 129 with flanged-on terminals 130, 131 at both ends. Running between these terminals may be two guide rails 128 on which a slide 183 moves. The slide 183 may be driven by the threaded rod 132. The rotation of the threaded rod 132 may be converted by a threaded sleeve incorporated in the slide 183 into a self-inhibiting translation. The threaded rod 132 may end on one side of the support structure in a bearing which is located in one of the two terminals 130, 131. The other terminal 130 may also be designed in substantially the same way, but to a certain extent may give the spindle clearance to the outside. On this part of the spindle, an end piece of an Oldham coupling 148 may be clamped on. The other end of the coupling may be clamped to the shaft of an electric motor 312. The motor 312 may be fastened in mechanical dampers 149. These, in turn, may be attached to a holder structure 136 including three plates perpendicular to each other. The holder structure may be screwed to the outer side of the terminal 130 which may assure access to the spindle. In this way, through rotation of the motor axle, the slide 183 can be moved linearly along the spindle axle.

Attached to the slide 183 may be a multiple-joint arm structure which may allow the holder unit 20 attached to the end effector to move in 5 degrees of freedom. Preferably, the first three axes of the articulated arm may be aligned in parallel. With these three axes, three of the degrees of freedom can already be set.

A bottom place (e.g., location) may be attached to the slide and perpendicularly thereto a base plate 184. It may comprise a gear module 187, which may be driven by an electric motor 310 and may have an integrated cross-roller bearing for diverting the forces and torques and may constitute the articulated joint 32. The plate structure 220 may be mounted on the end face of the gear output. Accommodated in a recess, this plate may have the circuit board 264 of the angle measuring system belonging to the articulated joint 32. At the upper end of the plate 220, there may be an electric motor 308 of the second articulated joint 34 on the same side as the gear output of the basic articulated joint 32. This may be attached by a flanged plate. Attached on the opposite side of the plate 220 may be the gear mechanism of the articulated joint 34. This may also be in contact with the end surface of the gear output on the plate 220. The plate 230 may be applied to the end surface of the drive of the gear mechanism. The board of the angle measuring system of articulated joint 34 may also be located in a corresponding recess on the other side of the plate 230, relative to the recess of the first-mentioned angle measuring system.

On the upper side of the plate 230, an electric motor 302 may be attached in the same alignment as the electric motor 308 of the articulated joint 34 by a flanged plate. In a position (e.g., substantially the same position) on the plate 230 on the opposite side, the output of the gear mechanism 187 of the articulated joints 36 may be fixed with its end surface on the plate 230. On the end surface of the drive wheel 187, a mounting plate 236 may be applied.

Attached to this at a right angle on the side of the gear mechanism 187 may be a further plate 237. This may provide a mounting for the, gear mechanism 187 that may be used downwards on the Z-axis of the device 10. Attached above this gear mechanism 187 by an adapter flange 245 may be a further electric motor 304 for actuating the articulated joint 36.

Furthermore, above the motor 304, a 6 DoF sensor with an operating element may be attached on a platform 251. The alignment of its axes corresponds to the arrangement of the X-axis, Y-axis and Z-axis of the device 10 in the normal state.

Under the gear mechanism 187 of the Z-axis, a mounting plate 256 may be perpendicularly attached on the end surface of the gear output. On its rear, the plate 256 may accommodate an electric motor 306 by a flanged plate. The shaft of this may be non-rotatably connected to a gear mechanism, the drive wheel of which may be fastened to the end surface of mounting plate 256. This combination may cause an adjustment of the articulated joint 36 about the Y-axis. On the output wheel of the latter gear mechanism may be a mounting plate 263, which may constitute the mechanical connection for the pin holder. The pin holder may initially include an external fixator configuration. This may include two rods 158 to which two Schanz screws 182 may be clamped by special clamping jaws 164. The two basic holders may be applied in a parallel manner. For example, the Schanz screws may be fixed in the clamping jaws perpendicularly to the two basic rods in a plane parallel to the plane through the two basic carriers.

Both Schanz screws may be screwed into the distal femur segment 272. For example, in the case of intramedullary nailing, the Schanz screws close to the fracture gap can be inserted mono-cortically. For insertion of the nail the medullary space may be free of obstacles.

To hold the basic rod system, the device 10 may have a clamping jaw holder, comprising a mountable cap 157 and a base plate 156 into which the cap 157 may be screwed.

By a transition piece 265, the base plate 156 may be attached on its underside at right angles to the mounting plate 263. For this, the transition piece 265 may have three drilled holes for assembly on said mounting plate 263 and two drilled holes perpendicular thereto for assembly of the base plate 156 of the pin holder.

Figure 13:
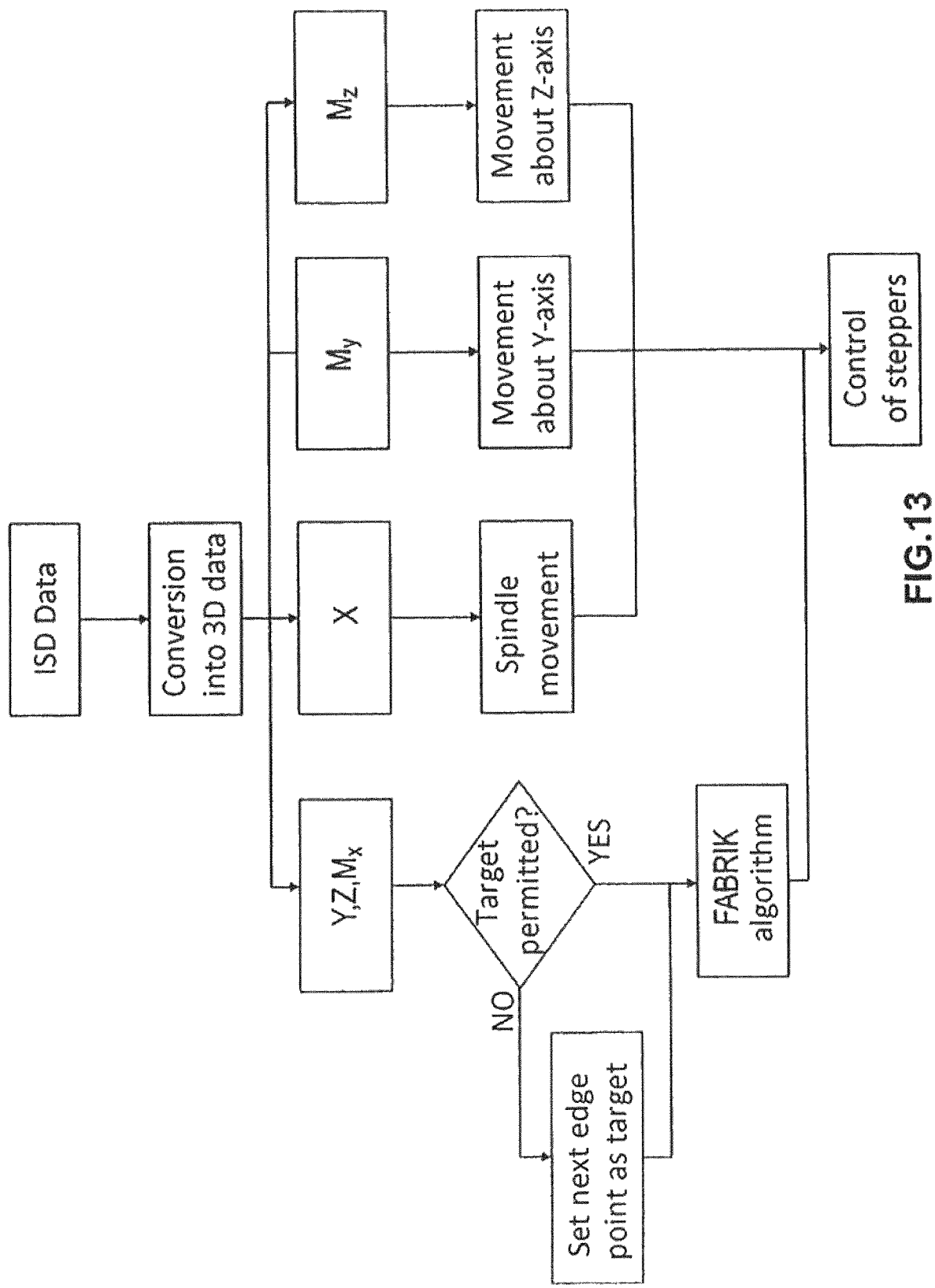
FIG. 13 shows a sequence plan for controlling the actuators for repositioning bone fracture fragments.

FIG. 13 illustrates a sequence plan for controlling the actuators for repositioning bone fracture fragments. In connection with operating input by way of the operating element 60, ISD data may be generated which are then converted into 3D data. When the device 10 is in operation, through applying power to the motors and through braking, a holding torque may be exerted in each articulated joint 32, 34, 36. This may result in (e.g., permanent) holding of the position and orientation of the pin holder and the Schanz screws connected thereto. For example, this also may result in the (e.g., permanent) retention of the distal femur fragment. If the user changes the position or orientation of the cap of the 6 DoF sensor, this may be converted into a movement. For example, operation by a user may be provided in a manner that is intuitive for the user.

If the user desires a translation of the pin holder in the positive X-direction, the user may push the operating element 60 with the cap 254 in this direction (e.g., via the user's hand on top of it). In this case, the user may directly implement control of the motor on the spindle. If the user desires a translation in the Z or Y-direction, the user may push the cap in one of these directions. This action may be implemented by the articulated joint arm structure. At this time, an inverse situation is involved. The translation that is known may be recorded in the 6 DoF sensor, but the angle settings are individually calculated. For this, an iterative process such as FABRIK may be used. The translation desired by the user may be delivered (e.g., as unit-less) by the sensor and converted into a speed. For the known duration of controlling the motor, the travelled path may be calculated and added to the position of the target point.

For controlling the motors 302 to 312, a speed trajectory may be generated. This may include a linear acceleration phase with a defined gradient until the maximum speed may be reached. It may be held until a linear deceleration ramp with a defined gradient sets in and the speed has fallen (e.g., fallen to zero).

If the user continues to maintain an input during the movement of the system, the start of the deceleration ramp may be recalculated and may be started correspondingly later if it has not for example yet been reached. If the system is already in the deceleration phase, an acceleration ramp suitable for reaching the maximum speed with a defined gradient may be calculated and implemented. If the user ends an entry, the previously calculated movement trajectory may run until completion. Thereafter the achieved positioning may be held (e.g., permanently held). The same procedure may apply to changing the alignment of the end effector. For example, the user may turn the cap 254 about at least one of the axes. If this is a rotation about the Y-axis or Z-axis—designated My and Mz—the relevant drive unit 302 to 306 of the articulated joint 36 may be directly actuated.

However, if this is a rotation about the X-axis designated Mx—, for example by the FABRIK algorithm a new configuration of the angle settings of the articulated arm may be calculated. The participating articulated joints may then be actuated as described. On completion of the process, the alignment and position of the end effector may be in turn held without user input.

An exemplary intraoperative use of the device 10 may take place as follows. First, the operator may fit each fragment with (e.g., two) Schanz screws. These can for example be inserted in one plane, and may or may not be parallel to each other. In addition, one screw may be inserted close (e.g., quite close) to the fracture gap and one screw (e.g., relatively far away) away from the fracture gap. In accordance with the procedure of applying an external fixator, the screws may be clamped onto two parallel rods with special clamping jaws. Via a clamp mounting, these rods may then be clamped onto the holder on the end effector of the relevant articulated arm.

Upon completion of these measures, the device 10 can be positioned and fixed on the operating table. Alternatively the device 10 can be fixed to the operating table before the start of positioning and at that point brought into operation. The passive, first articulated arm may be initially brought into position and manually fixed. The active, second articulated arm may then be moved into the desired position through input via the sensor element. Via the screw clamping, the rods of the external fixator configuration may be connected with the end effector of the relevant articulated arm. For this, the rods may be moved into the basic shell of the clamping device, the clamping cap may be positioned above them and both may be pulled toward each other through turning of the centrally arranged screw.

If a play-free mechanical clamping connection is created, the operator can loosen individual joints of the passive arm and newly align the proximal fragment. After suitable (e.g., satisfactory) alignment, the arm may be completely fixed. The thus produced retention of the position and orientation of the proximal fragment may serve as a reference for the alignment and positioning of the distal fragment. For this, the operator may use the motorized articulated arm and may change the alignment and position of the end effector through acting on the sensor cap by the user's hand placed on it. After suitable (e.g., satisfactory) alignment, the operator may release the sensor. The device now may keep the set position and orientation constant. By way of for example X-ray imaging, the operator can check the suitability of the repositioning. Therein, for protection against radiation exposure, the entire operating team can assume a suitable (e.g., certain or predetermined) distance from the radiation beam. After evaluation of the produced images, corrections can be carried out through renewed positioning. On completion of the positioning, the guide wire can be introduced and, if applicable, the medullary space drilled open. If nail application is being carried out without drilling open and without guide wire, the nail can inserted at this point. After the nail has passed the fracture gap the device is removed. This may be done in reverse order to the application of the device. First, the clamping connection with the device with the external fixator may be loosened, and the Schanz screws may then be removed. Finally, the procedure may then be ended in that the nail is fully inserted in a suitable manner, locked, and the closing cap applied (e.g., if appropriate) and wounds may be closed. When plating the fragments, the device may remain in place during this stage of treatment. Through the above-described device, an increase in the precision of positioning the bone may be achieved, In at least some exemplary embodiments, parts of the operator's body may not remain in the radiation beam of an X-ray device during the process of producing the X-ray images. Furthermore, the operator may be able to intuitively control the described system.

Although robotic systems may be controlled by joysticks firmly fixed in space, in at least some exemplary embodiments the sensor may be located directly on the end effector. For example, the surgeon or the assistant physician may cover with one hand the area of the extremity is distal of the fracture and with the other hand the sensor element which is arranged (e.g., very close) close to the extremity and undergoes no movement relative to the extremity. In this way, the physician can move the area of the extremity in the same way as he would do without using the device. This procedure is intuitive and does not require long learning/training times/efforts by operators. A further advantage may be that the physician has a hand on the extremity at some, most, or all times and therefore may receive (e.g., permanent) haptic feedback in the same way as the user would in purely manual repositioning, with the advantage that no high tensile forces are applied to the extremity. Through the decoupling of the high tensile force produced by the patient's muscles, very delicate and precise work can be carried out, which is associated with a better outcome. Moreover, the device 10 may be portable, small and light in weight, can be mounted on the universal rail of an operating table or the leg plate interface of an operating table and may allow integration into leg plates.

Device 10 may involve no navigation and/or initialization, no current CT data for the patient and no specially-trained personnel. Over and beyond this, the method is considerably less costly and time-consuming and allows intuitive control of the system.

It will be apparent to those skilled in the art that various modifications and variations can be made to the disclosed method and apparatus. Other embodiments will be apparent to those skilled in the art from consideration of the specification and practice of the disclosed method and apparatus. It is intended that the specification and the disclosed examples be considered as exemplary only, with a true scope being indicated by the following claims.

What is claimed is:

1. A device for repositioning bone fracture fragments, comprising:
    a carrier assembly;
    a first arm assembly attached to the carrier assembly, the first arm assembly configured to hold a first bone fracture fragment;
    a second arm assembly comprising a first end attached to the carrier assembly, and a second end extending away from the carrier assembly, the second end having a holder assembly that is configured to hold at least one Schanz screw to hold a second bone fracture fragment;
    an actuator assembly configured to adjust the second arm assembly; and
    an operating assembly configured to control an adjustment of the second arm assembly via the actuator assembly;
    wherein the operating assembly is a manually operable operating assembly disposed in a region of the second end of the second arm assembly and configured to undergo no movement with respect to the holder assembly of the second arm assembly, or with respect to the at least one Schanz screw when present, when the second arm assembly is adjusted via the actuator assembly.

2. The device according to claim 1, wherein:
    a first holder assembly configured to hold a Schanz screw is provided on an end portion of the first arm assembly facing away from the carrier assembly.

3. The device according to claim 1, wherein via the actuator assembly, the second arm assembly is adjustable so that a position of the holder assembly relative to the carrier assembly is adjustable in a plurality of directions resulting from user contact with the operating assembly.

4. The device according to claim 1, wherein the second arm assembly is adjustable via the actuator assembly so that a position and an alignment of the holder assembly with respect to a second holder assembly not mounted on the second arm assembly is adjustable about six degrees of freedom.

5. The device according to claim 1, wherein both the holder assembly and a distal arm segment are located at the second end of the second arm assembly facing away from the carrier assembly;
    one or more additional arm segments are disposed between the distal arm segment and the carrier assembly; and
    wherein the operating assembly is located at the distal arm segment such that upon operation of a sensor of the operating assembly, corresponding movement occurs among the operating assembly, the distal arm segment, and the holder assembly.

6. The device according to claim 1, wherein the operating assembly comprises a sensor cap disposed at the region of the second end of the second arm assembly.

7. The device according to claim 1, further comprising a first holder assembly located at an end portion of the first arm assembly facing away from the carrier assembly, wherein the at least one manually adjustable articulated joint is configured so that the first holder assembly is adjustable about six degrees of freedom via the first arm assembly.

8. The device of claim 1, wherein the operating assembly is configured to move the holder assembly and the at least one Schanz screw when present with respect to the first arm assembly via the actuator assembly.

9. The device of claim 1, wherein the first arm assembly is adjustable and lockable independent of the second arm assembly.

10. A device for repositioning bone fracture fragments, comprising:
    a carrier assembly fastenable to an operating table and including a rail member;
    a first arm assembly attached to the carrier assembly, the first arm assembly configured to hold a first bone fracture fragment;
    a second arm assembly attached to the carrier assembly, the second arm assembly comprising: a first articulated joint, a second articulated joint, a third articulated joint, a first connection plate, and a second connection plate; the first articulated joint is attached to the carrier assembly; the first connection plate is disposed between the first articulated joint and the second articulated joint; the second connection plate is disposed between the second articulated joint and the third articulated joint; and a holder assembly disposed on the third articulated joint is configured to hold a second bone fracture fragment;

an actuator assembly configured to adjust the second arm assembly; and an operating assembly configured to control an adjustment of the second arm assembly via the actuator assembly, the operating assembly disposed on the second arm assembly in a region of the third articulated joint such that the operating assembly is configured to undergo no movement with respect to the holder assembly of the second arm assembly when the second arm assembly is adjusted via the actuator assembly, and such that the operating assembly and the holder assembly move together with respect to the first arm assembly, and also with respect to the operating table when present, when the operating assembly activates the actuator assembly.

11. The device according to claim 10, wherein the operating assembly comprises a six degree of freedom sensor comprising a sensor cap or a joystick.

12. The device according to claim 10, wherein the operating assembly when actuated by user hand contact causes corresponding translation movement of both the operating assembly and the holder assembly.

13. The device of claim 10, wherein the operating assembly and the holder assembly move together with respect to the operating table, when present, when the operating assembly actives the actuator assembly by causing the slide member to move in a longitudinal direction of the rail member.

14. An operating table, comprising:
a table portion having a leg supporting surface, the leg supporting surface being for supporting a patient's leg when present; and
a device for repositioning bone fracture fragments, including:
a carrier assembly including a fastening assembly configured to fasten the device to the table portion;
a first arm assembly attached to the carrier assembly, the first arm assembly configured to hold a first bone fracture fragment;
a second arm assembly comprising a first end attached to the carrier assembly and a second end extending laterally over the leg supporting portion, the second end having a holder assembly that is configured to hold a second bone fracture fragment;
an actuator assembly configured to adjust the second arm assembly; and
a manually operable operating assembly located on the second end of the second arm assembly and configured to control an adjustment of the second arm assembly via the actuator assembly such that the operating assembly undergoes no movement with respect to the holder assembly of the second arm assembly when the second arm assembly is adjusted via the actuator assembly; and
wherein the second arm assembly, the holder assembly, and the operating assembly undergo movement via the actuator assembly with respect to the first arm assembly, and with respect to the leg supporting surface, upon operation of the operating assembly.

15. The operating table according to claim 14, wherein the leg supporting portion comprises at least one of a patient upper leg cushion or a patient lower leg cushion and at least one of the patient upper leg cushion or the patient lower leg cushion is detachably fastened to the carrier assembly.

16. The operating table according to claim 14, wherein the operating assembly is responsive to a first type of manual contact to cause corresponding translational movement of at least a portion of the second arm assembly and a second type of manual contact to cause corresponding rotation of the same portion of the second arm assembly.

17. The operating table of claim 14, wherein the carrier assembly includes a rail member;
wherein the second arm assembly includes a slide member that is disposed on the rail member; and
wherein the second arm assembly and the operating assembly undergo longitudinal movement with respect to the leg supporting surface upon operation of the operating assembly via the actuator assembly causing the slide member to move in a longitudinal direction of the rail member.

18. A device for repositioning bone fracture fragments, comprising:
a first arm assembly comprising a first end and a second end, the first arm assembly configured to hold a first bone fracture fragment at the second end of the first arm assembly via a first bone fragment holding assembly;
a second arm assembly comprising a first end and a second end, the second arm assembly spaced apart from the first arm assembly and configured to hold a second bone fracture fragment at the second end of the second arm assembly via a second bone fragment holding assembly;
an operating assembly operatively connected to an actuator assembly to control one or more motors which in turn adjust the position and/or orientation of the second end of the second arm assembly with respect to a the second end of the first arm assembly via user hand contact applied to the operating assembly;
wherein the operating assembly is disposed at a distal region of the second arm assembly such that the operating assembly undergoes no movement with respect to the second bone fragment holding assembly of the second arm assembly when the second arm assembly is adjusted via the actuator assembly.

19. The device of claim 18, wherein the operating assembly is a sensor associated with a plurality of degrees of freedom, and wherein operation of the sensor about a first degrees of freedom causes corresponding movement of the second arm in the first degree of freedom.

20. The device of claim 19, wherein the sensor is associated with six degrees of freedom.

21. The device of claim 18, wherein the second arm assembly comprises:
a first joint located at the carrier assembly, a distal joint located towards a distal end of the second arm assembly where the second arm assembly is configured to hold the second bone fracture fragment, and at least one arm segment located between the first joint and the distal joint;
wherein the operating assembly is disposed in the region of the distal joint of the second arm assembly.

* * * * *